(12) United States Patent
Lyon

(10) Patent No.: US 10,458,975 B1
(45) Date of Patent: Oct. 29, 2019

(54) CALIBRATION DEVICE AND METHOD FOR CALIBRATING AN IGNITION INTERLOCK DEVICE

(71) Applicant: Michael Lyon, Redlands, CA (US)

(72) Inventor: Michael Lyon, Redlands, CA (US)

(73) Assignee: 1A Smart Start, LLC, Grapevine, TX (US)

( * ) Notice: Subject to any disclaimer, the term of this patent is extended or adjusted under 35 U.S.C. 154(b) by 778 days.

(21) Appl. No.: 14/706,402

(22) Filed: May 7, 2015

Related U.S. Application Data

(63) Continuation-in-part of application No. 14/036,343, filed on Sep. 25, 2013, now abandoned, and a continuation-in-part of application No. 13/955,260, filed on Jul. 31, 2013, now Pat. No. 9,772,318.

(51) Int. Cl.
*G01N 33/497* (2006.01)
*G01N 33/00* (2006.01)
*B60K 28/06* (2006.01)

(52) U.S. Cl.
CPC ....... *G01N 33/4972* (2013.01); *B60K 28/063* (2013.01); *G01N 33/0036* (2013.01)

(58) Field of Classification Search
None
See application file for complete search history.

(56) References Cited

U.S. PATENT DOCUMENTS

| | | |
|---|---|---|
| 3,780,311 A | 12/1973 | Brown |
| 3,824,167 A * | 7/1974 | Oswin et al. ............ G01N 1/34 |
| | | 204/411 |
| 3,824,537 A | 7/1974 | Albertson |
| 3,831,707 A | 8/1974 | Takeuchi |
| 3,948,604 A | 4/1976 | Hoppesch |
| 4,278,636 A | 7/1981 | Voigt et al. |
| 4,391,777 A | 7/1983 | Hutson |
| 4,407,152 A | 10/1983 | Guth |
| 4,487,055 A | 12/1984 | Wolf |
| 4,592,443 A | 6/1986 | Simon |

(Continued)

FOREIGN PATENT DOCUMENTS

| | | |
|---|---|---|
| GB | 2029717 B | 8/1982 |
| KR | 20060111799 A | 10/2006 |

(Continued)

OTHER PUBLICATIONS

"Lion Alcolmeter SD-400", User Handbook: General, Issue 7, Lion Laboratories Limited, 2012, 37 pages.

(Continued)

*Primary Examiner* — Robert K Carpenter
(74) *Attorney, Agent, or Firm* — Slater Matsil, LLP

(57) ABSTRACT

An interlock data collection and calibration system has a device computer, and a gas sample delivery system for delivering a first gas sample and a second gas sample to the ignition interlock device, the first and second gas samples having different predetermined concentrations of alcohol. The device computer includes a calibration program for calibrating the ignition interlock device using the first gas sample, and then delivering the second gas sample to the ignition interlock device to verify that the ignition interlock device correctly determines the second alcohol concentration of the second sample gas.

9 Claims, 5 Drawing Sheets

(56) References Cited

U.S. PATENT DOCUMENTS

| | | |
|---|---|---|
| 4,678,057 A | 7/1987 | Elfman et al. |
| 4,697,666 A | 10/1987 | Collier |
| 4,749,553 A | 6/1988 | Lopez et al. |
| 4,770,026 A | 9/1988 | Wolf |
| 5,422,485 A | 6/1995 | Bowlds |
| 5,443,794 A | 8/1995 | Williams |
| 6,026,674 A | 2/2000 | Gammenthaler |
| 6,096,558 A | 8/2000 | Stock |
| 6,167,746 B1 | 1/2001 | Gammenthaler |
| 6,442,639 B1 | 8/2002 | McElhattan et al. |
| 6,526,802 B1 * | 3/2003 | Fisher ............... G01N 33/4972 366/273 |
| 6,792,793 B2 | 9/2004 | Mendoza |
| 6,853,956 B2 | 2/2005 | Ballard, Jr. et al. |
| 6,956,484 B2 | 10/2005 | Crespo |
| 6,967,581 B2 | 11/2005 | Karsten |
| 7,204,335 B2 | 4/2007 | Stewart et al. |
| 7,422,723 B1 | 9/2008 | Betsill |
| 7,451,852 B2 | 11/2008 | Stewart et al. |
| 7,488,229 B2 | 2/2009 | Ben-Oren et al. |
| 7,541,192 B2 | 6/2009 | Stock |
| 7,543,472 B2 | 6/2009 | Crespo et al. |
| 7,895,878 B1 | 3/2011 | Guth et al. |
| 8,059,003 B2 | 11/2011 | Roth |
| 8,240,419 B2 | 8/2012 | Zimmermann et al. |
| 8,418,523 B2 | 4/2013 | Lueck et al. |
| 8,515,704 B2 | 8/2013 | Son et al. |
| 8,590,364 B2 | 11/2013 | Lopez et al. |
| D708,757 S | 7/2014 | Shibata |
| 8,878,669 B2 | 11/2014 | Nothacker et al. |
| 9,020,773 B2 | 4/2015 | Son et al. |
| 9,207,223 B2 | 12/2015 | Arias et al. |
| 9,772,318 B1 | 9/2017 | Lyon |
| 2003/0000281 A1 | 1/2003 | Ketler et al. |
| 2003/0167821 A1 | 9/2003 | Sussman et al. |
| 2005/0241871 A1 | 11/2005 | Stewart et al. |
| 2006/0078467 A1 | 4/2006 | Stock |
| 2007/0044534 A1 | 3/2007 | Forrest |
| 2007/0144812 A1 | 6/2007 | Stewart et al. |
| 2009/0004054 A1 | 1/2009 | Burke et al. |
| 2009/0056408 A1 | 3/2009 | Tryfonos et al. |
| 2009/0205407 A1 | 8/2009 | Marhefka et al. |
| 2009/0278656 A1 | 11/2009 | Lopez et al. |
| 2010/0012417 A1 | 1/2010 | Walter et al. |
| 2010/0081909 A1 | 4/2010 | Budiman et al. |
| 2010/0108425 A1 | 5/2010 | Crespo et al. |
| 2010/0223975 A1 | 9/2010 | Lueck et al. |
| 2010/0314190 A1 | 12/2010 | Zimmermann et al. |
| 2013/0282321 A1 | 10/2013 | Son et al. |
| 2013/0308151 A1 | 11/2013 | Kobayashi et al. |
| 2014/0041436 A1 | 2/2014 | Knott et al. |
| 2014/0061042 A1 | 3/2014 | Ofir et al. |
| 2014/0335905 A1 | 11/2014 | Bhoot |
| 2014/0358020 A1 | 12/2014 | Park et al. |
| 2015/0164373 A1 | 6/2015 | Davis et al. |

FOREIGN PATENT DOCUMENTS

| | | | |
|---|---|---|---|
| KR | 20100070199 A | * | 6/2010 |
| KR | 101003385 B1 | | 12/2010 |
| KR | 101059977 B1 | | 8/2011 |
| KR | 101059978 B1 | | 8/2011 |
| KR | 101174373 B1 | | 8/2012 |
| WO | 9714947 A2 | | 4/1997 |
| WO | 2009111484 A3 | | 9/2009 |
| WO | 2011143693 A1 | | 11/2011 |

OTHER PUBLICATIONS

Alco-Sensor FST Operators Manual, Intoximeters, Inc., St. Louis, MO, Jun. 2007, 37 pages.

Drager X-am 2500 (MQG 0011) Technical Manual, Nov. 2012, 36 pages.

Intox EC/IR II, Intoximeters Inc., Nov. 2007, 2 pages.

Lifeloc Professional Breath Alcohol Tester, Lifeloc FC10 Operations Manual, Unlock the Power of Alcohol Testing, 27 pages.

* cited by examiner

CALIBRATION DEVICE AND METHOD FOR CALIBRATING AN IGNITION INTERLOCK DEVICE

CROSS-REFERENCE TO RELATED APPLICATIONS

This application for a utility patent is a continuation-in-part of previously filed utility patent applications, both currently pending, having application Ser. No. 14/036,343, filed Sep. 25, 2013, and Ser. No. 13/955,260, filed Jul. 31, 2013.

BACKGROUND OF THE INVENTION

Field of the Invention

This invention relates generally to ignition interlock devices, and more particularly to an interlock data collection and calibration system for automatically calibrating a ignition interlock device, and for verifying that the calibration was successful.

Description of Related Art

Driving under the influence of alcohol is a well known safety hazard, which causes thousands of deaths per year in the United States alone. To address this problem, states have established laws that criminalize operation of a vehicle and other machinery with a blood alcohol concentration ("BAC") greater than a preset value (e.g., 0.08% BAC).

To reduce the rate of recidivism of driving under the influence, many states require the installation of devices in the vehicles and other machinery of individuals convicted of driving under the influence of alcohol. Such devices, which are commonly referred to as breath alcohol ignition interlock devices ("IID"). These IIDs have been developed to be directly connected to a vehicle's ignition system and are designed to prevent automobiles and other machinery from being operated by inebriated individuals.

IIDs typically include semiconductor sensors, commonly referred to as a Taguchi cell, and/or electrochemical cells, infrared sensors, or equivalent devices, to sense and quantify the amount of alcohol in a driver's breath. Most modern IIDs use an ethanol-specific fuel cell for a sensor. Examples of these sensors are shown in U.S. Pat. Nos. 4,487,055, 6,026,674, 6,167,746, and/or 7,204,335, which are hereby incorporated by reference.

As described in the noted patents, a fuel cell sensor is an electrochemical device in which alcohol undergoes a chemical oxidation reaction at a catalytic electrode surface (i.e., platinum, etc.) to generate an electric current. This current is then measured and converted to an alcohol equivalent reading. Although fuel cell technology is not as accurate or reliable as infrared spectroscopy technology used in evidentiary breathalyzers, they are less expensive and specifically tailored to quantify ethyl alcohol (drinking alcohol). Among manufacturers of IIDs are Smart Start Inc., LifeSafer Interlock, SOS, Ignition Interlock Systems, Intoxalock and Monitech.

Typically, in order to start a vehicle equipped with an IID, the driver must first blow into the breath analyzer installed in the vehicle or machinery. Conventional IIDs measure the alcohol content of the breath (BrAC) and use this information to determine the driver's BAC. If the driver's BAC is determined to exceed a preset limit, the vehicle's ignition is disabled and the vehicle is rendered inoperable. If the driver's BAC is determined to be below the preset limit, ignition is permitted and the vehicle may be started. Exemplary ignition interlock devices that utilize breath analyzers are described in, for example, U.S. Pat. Nos. 3,780,311, 3,824,537, 3,831,707, 4,592,443, and 4,697,666.

Generally, the methods for detecting BrAC, for and using ignition interlock systems to prevent automobiles and other machinery from being operated by inebriated individuals, are well known in the art. Moreover, the current invention does not rely on any particular ignition interlock device or method for testing BrAC, but instead can be universally applied to any ignition interlock data retrieved from any ignition interlock device installed on any vehicle or equipment, and also used on related and equivalent devices, such as breathalyzers and similar devices.

The prior art also teaches systems for reporting IID data to a central server. Roth, U.S. Pat. No. 8,059,003, teaches a system and method for collecting data from IID, and uploading the data to a central server. This reference teaches the use of encryption and date stamping to provide reliable evidence regarding the use of the IID, for use in courts. The above-described references are hereby incorporated by reference in full.

SUMMARY OF THE INVENTION

The present invention teaches certain benefits in construction and use which give rise to the objectives described below.

The present invention provides an interlock data collection and calibration system for calibrating an ignition interlock device. The system includes a device computer, and a gas sample delivery system for delivering a first gas sample and a second gas sample to the ignition interlock device, the first and second gas samples having different predetermined concentrations of alcohol. The device computer includes a calibration program operably installed on a computer memory of the device computer for directing the sample gas delivery system to deliver the first sample gas to the ignition interlock device, calibrating the ignition interlock device, directing the sample gas delivery system to deliver the second sample gas to the ignition interlock device, and confirming that the ignition interlock device correctly determines the second alcohol concentration of the second sample gas, thereby confirming that the ignition interlock device is correctly calibrated.

A primary objective of the present invention is to provide a calibration device and a method for calibrating an ignition interlock device having advantages not taught by the prior art.

Another objective is to provide a calibration device for calibrating an ignition interlock device that provides two different samples of sample gasses, each having a different concentration of alcohol, for reliable calibration of the ignition interlock device, and for verifying that the calibration was successful.

Another objective is to provide a calibration device for calibrating an ignition interlock device that is completely automated, traceable, and reliable.

Another objective is to provide a method for calibrating an ignition interlock device that is able to automatically gather, reprogram, document, and store data related to the calibration and use of the interlock data collection and calibration system for evidentiary purposes.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, an interlock data collection and calibration system 10 ("IDCCS") for use with an ignition interlock device 12 ("IID"). The IDCCS 10 is used to calibrate the IID 12, and to receive, upload to, and store data from the IID 12 in a local database 118. The contents of the local database 118 may also be uploaded to a central database 138, as discussed in greater detail below.

Figure 1:
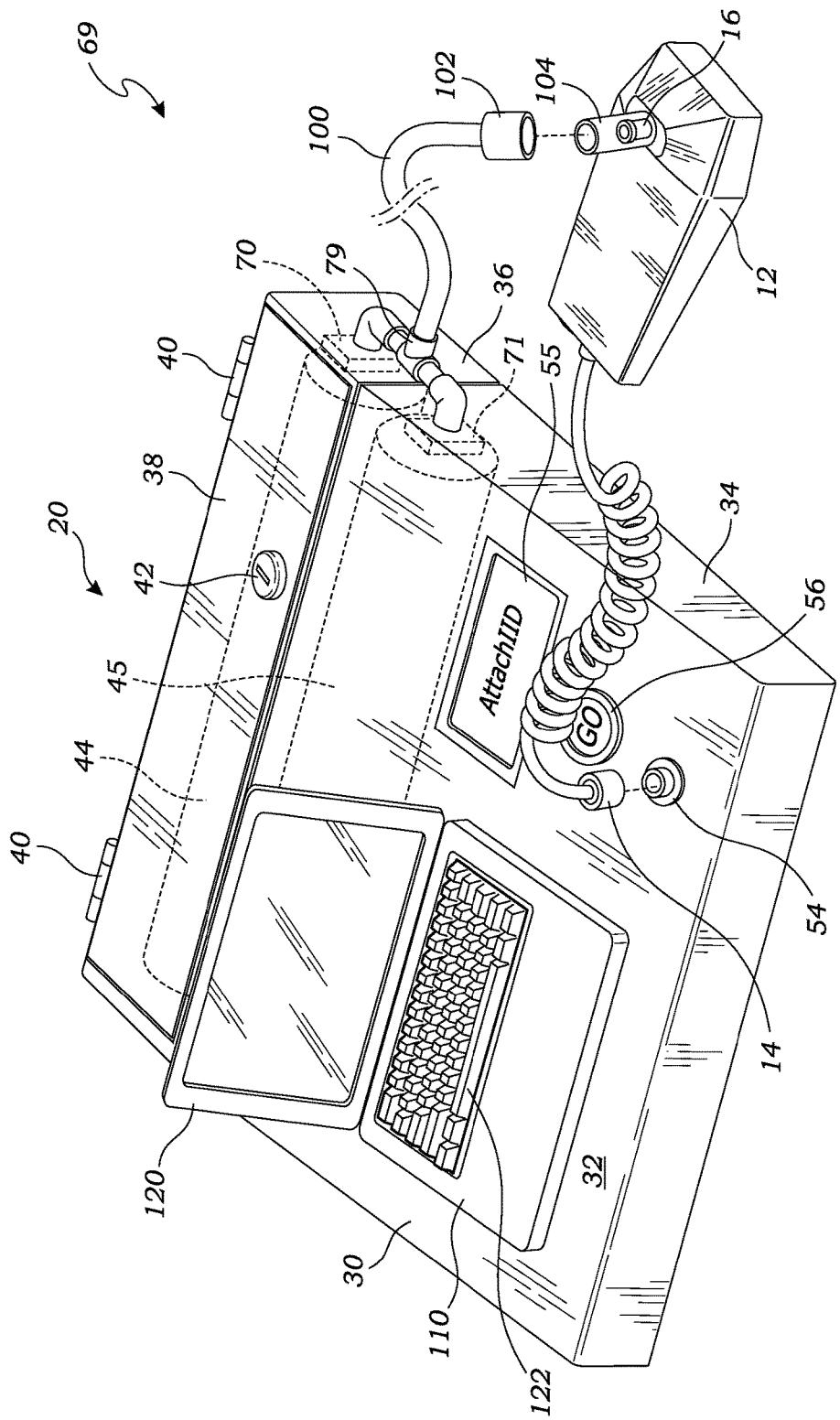
FIG. 1 is a perspective view of one embodiment of an interlock data collection and calibration system.
Figure 2:
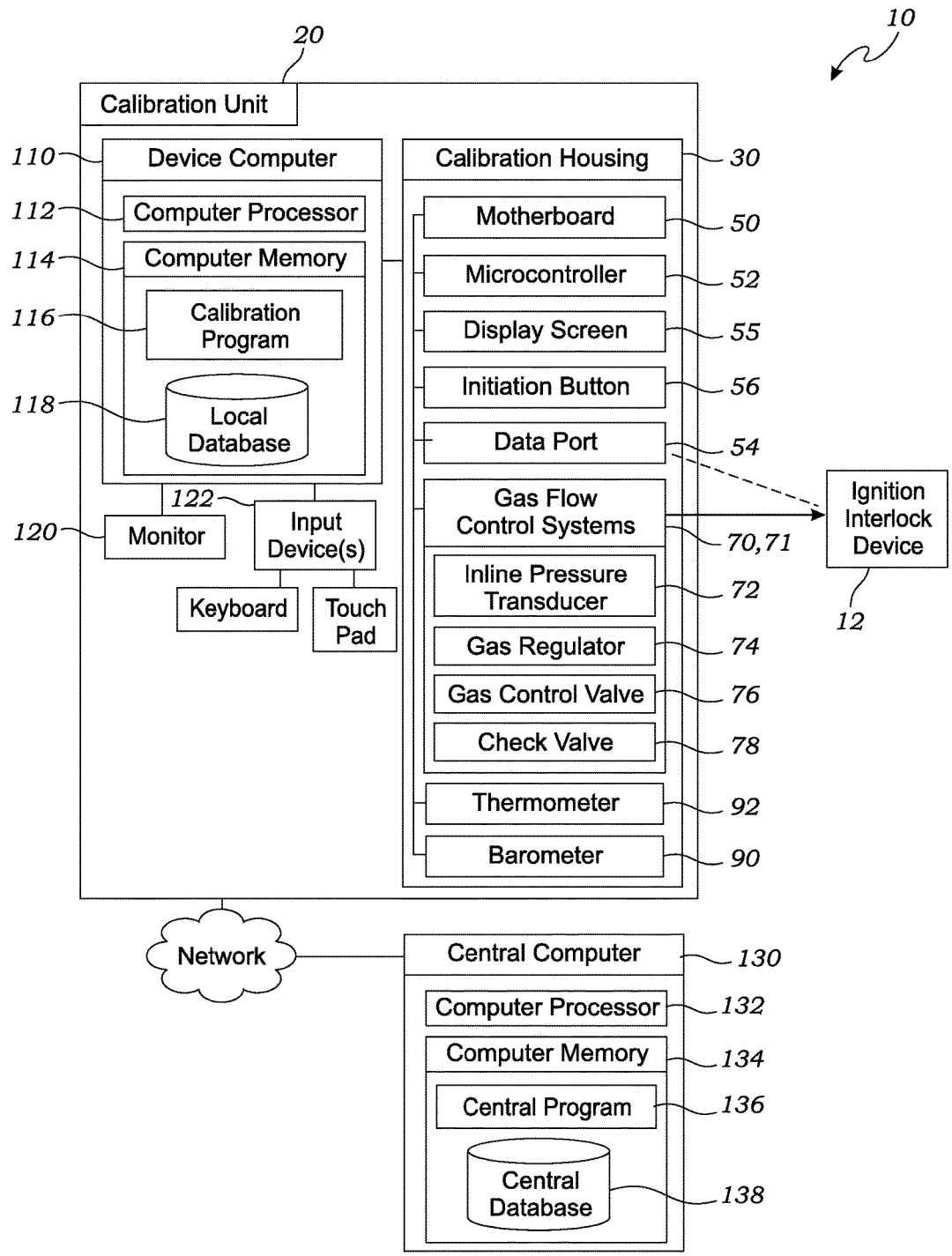
FIG. 2 is a block diagram of the interlock data collection and calibration system of FIG. 1, illustrating a first embodiment of a gas sample delivery system.

FIG. 1 is a perspective view of one embodiment of the IDCCS 10. FIG. 2 is a block diagram of the IDCCS 10 of FIG. 1. As illustrated in FIGS. 1 and 2, the IDCCS 10 includes a calibration unit 20 that is adapted to be connected with the IID 12 for calibrating the IID 12. The calibration unit 20 includes a calibration housing 30 and a device computer 110. While the calibration housing 30 and the device computer 110 are illustrated as two separate units in this embodiment, they could also be integrated into a single unit, in an alternative embodiment, wherein operable components of the device computer 110 are incorporated into the calibration housing 30.

In the embodiment of FIG. 1, the calibration housing 30 is a generally rectangular housing that is built to contain and protect the various electronic components described below. The calibration housing 30 may include a top surface 32, side walls 34, and a rear chamber 36 that includes a cover 38, attached with a hinge 40 and a latch element 42 (in this case, a lock), for covering the rear chamber 36. In this embodiment, the rear chamber 36 is shaped to contain a gas sample delivery system 69, which in this embodiment includes one or more sources of sample gas, in this case gas cylinders 44 and 45. The at least one gas source may be operably connected to the rest of the gas sample delivery system 69 using any form of coupling known in the art, in this case via the regulators and valves described in more detail below.

In the embodiment of FIG. 1, two gas cylinders 44 and 45 are used as the source of the sample gasses. In alternative embodiments, a single gas cylinder 44 may be used; or other gas sources may be used, such as wet bath system, or any other sources know to those skilled in the art. While some embodiments of the calibration housing 30 are illustrated, those skilled in the art may devise alternative structures, and such alternatives should be considered within the scope of the present invention.

The gas sample delivery system 69 functions to provide two different samples of sample gas, at different concentrations, so that the system 10 can be most reliably calibrated. As discussed in more detail below, the two different gas samples can come from two different sources, or a single source which is selectively diluted or otherwise changed.

In the embodiment of FIGS. 1 and 2, the gas sample delivery system 69 includes two gas cylinders 44 and 45, which each include sample gasses which include different concentrations of alcohol. The first gas cylinder 44 installed in the calibration housing 30 is for holding a prefilled gas for use in calibrating the calibration unit 20. The gas contains a predetermined amount of alcohol, for the purposes of calibrating the IID 12. In one embodiment, a first gas stored in the gas cylinder 44 may have a predetermined alcohol concentration, in this case of 0.08% per unit volume of gas. The second gas cylinder 45 may hold a second gas having an alcohol concentration of 0.02% of per unit volume of gas (or other predetermined concentration which may be selected by one skilled in the art. For ease of reference, alcohol concentrations of the first gas (0.08% per unit volume of gas) and the second gas (0.02% per unit volume of gas) hereinafter will be referred to as 0.08 g/dL and 0.02 g/dL respectively. Such use of the first gas and the second gas may allow calibrating the IID 12 for different alcohol concentrations (in this case ranging from approximately 0.08 g/dL to 0.02 g/dL, although other concentrations may be used). For purposes of this application, the term "approximately" is defined to mean +/−10%.

In some embodiments, the calibration housing 30 may be adapted to contain additional gas cylinders so that there are spare gas cylinders available readily at hand, and/or for providing third or more gas samples for further calibration steps (if desired). Each such additional gas cylinder may be prefilled with a gas having a predetermined alcohol concentration such as those discussed above. One ordinarily skilled in the art will understand that other alcohol concentrations may be used for calibrating the IID 12.

The gas cylinders 44 may be connected to respective gas delivery systems through which the gas may be released. For example, the gas cylinders 44, 45 may be connected to gas delivery systems 70, 71 respectively, described in greater detail below.

The gas cylinders 44 in the present embodiment are shown contained within the calibration housing 30, however in an alternate embodiment they may also be attached externally, or operably connected in some other manner. While the gas cylinders 44 are illustrated, in an alternate embodiment the gas cylinders 44 and 45 may be replaced by a "wet media" or "wet bath" system, or another system for delivering the sample gas. In that embodiment, a couple of containers (not shown), each containing water with ethanol or another alcohol solution dissolved at a known concentration, e.g., ranging from approximately 0.08 g/dL to 0.02 g/dL, within the water; and air is delivered at a specific flow rate through the solution to simulate the absorption of alcohol into the exhaled breath of a customer.

Figure 5:
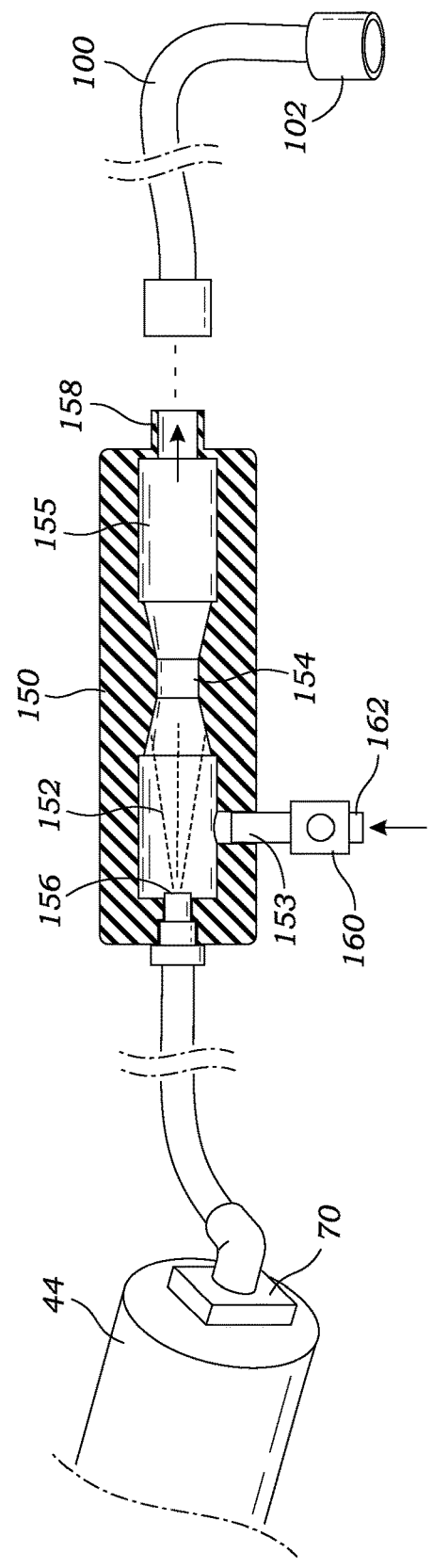
FIG. 5 is a perspective view of an alternative embodiment of the gas sample delivery system of FIG. 1, including a venturi vacuum pump.

In another embodiments, illustrated in FIG. 5, the calibration housing 30 may contain only one gas cylinder 44 (although further cylinders may be included as spares). In this embodiment, the sample gas provided from the gas cylinder 44 may be diluted, so as to provide two different sample concentrations. This option is discussed in greater detail below.

In the embodiment of FIGS. 1 and 2, the calibration housing 30 contains a motherboard 50, a microcontroller 52 connected to the motherboard 50, and a data port 54 also connected to the motherboard 50. The motherboard 50 is used to seat the microcontroller 52, and to also interconnected with the device computer 110 (or to seat the operably components thereof), as well as any integrated circuitry, computer chips, peripherals such as I/O ports and their associated devices, and any other components that may be desired. In the present embodiment the motherboard 50 is also connected to the gas delivery systems 70.

The microcontroller 52 controls the interaction between other components of the calibration housing 30, such as a display screen 55, an initiation button 56, the gas delivery systems 70, and the data port 54. As used in this application, the term "microcontroller" is hereby defined to include any form of processor and memory, integrated or apart, that can function to enable the operation of the IDCCS. The microcontroller 52 may also be connected to interface with an external device such as a personal computer, or any other device capable of interfacing with the calibration unit 20, via any form of wired or wireless connection known in the art.

The data port 54 is shaped and adapted for connecting the IDCCS 10 to the IID 12 to receive the data from the IID 12 for analysis. The data port 54 is operatively positioned on the calibration housing 30 for connection with a data plug 14 of the IID 12, either directly or via an adaptor (not shown) that enables the data port 54 to accept the data from a wider range of IID 12 output connections. Some examples of the data port 54 types are USB, DVI, VGA, and coaxial ports, although any similar or equivalent ports may also be used.

The display screen 55 is used for communicating information to the user, such as device status, instructions, error codes, and/or other similar information. The display screen 55 is operatively mounted on the calibration housing 30, in this embodiment on the top surface 32, to allow the user to read the display screen 55 during use of the IDCCS 10. The display screen 55 may be any form of display known in the art (e.g., liquid crystal display, digital, or their equivalents).

Also located operatively on the calibration housing 30 is the initiation button 56 which is used to initiate a manual calibration procedure or when so directed by the device computer 110. The initiation button 56 is hereby defined to include any form of button, switch, turnkey, touchscreen, voice activation, or similar/equivalent device or any other method of actuation known in the art. In the present embodiment, the initiation button 56 is a normally OFF button which when pressed initiates the calibration procedure and then returns to an OFF state. Other embodiments could include a button that remains in the ON state until the end of the calibration procedure or include intermediate states, such as a three-way switch if a stand-by or warm-up mode is desired.

The IDCCS 10 may also include a barometer 90 for the monitoring of the ambient air pressure, so that the local air pressure must be taken into account when generating a prescribed concentration of alcohol vapor for use in the calibration procedure and generating blood alcohol content equivalents for calibration of the IID, as discussed in greater detail below. This information may also be manually inputted, so that a barometer would not be required.

In this embodiment, the IDCCS 10 may also include a temperature sensor 92 for measuring the local temperature, as the temperature is also a factor in getting a proper reading of the IID 12. Temperature information may also be inputted manually, if desired.

In the embodiment of FIGS. 1 and 2, the gas delivery systems 70 and 71 function to deliver samples of gas from one of the gas cylinders 44 or 45 to the IID 12. For ease of explanation, only the gas delivery system 70 of the gas cylinder 44 is discussed below. However, one ordinarily skilled in the art will appreciate that the gas cylinder 45 may employ a similar gas delivery system such as a gas delivery system 71 having similar components that operate in a similar manner.

The gas delivery system 70 may include, in the present embodiment, an inline pressure transducer 72, a gas regulator 74, a gas control valve 76, and a check valve 78. The operation of the gas delivery system 70 is controlled by the microcontroller 52. When the microcontroller 52 is given the command to open the gas control valve 76, the gas control valve 76 opens and releases gas from the gas cylinder 44, through the gas control valve 76, the gas regulator 74, the check valve 78, to the IID 12 via a sample flow tube 100.

The inline pressure transducer 72 monitors the pressure in the gas cylinder 44. A low reading of the inline pressure transducer 72 could indicate a leak, faulty installation of the gas cylinder 44, or a depleted gas cylinder 44. The inline pressure transducer 72 can consist of any analog or digital gauge capable of measuring the pressure in the gas cylinder 44 and transmitting the data to the device computer 110 for monitoring and analysis. Types of inline pressure transducers 72 that could be used include, without limitation, piezoresistive strain gauges, electromagnetic, or potentiometric.

The gas regulator 74 is used to reduce the gas pressure from the gas cylinder 44 to a desired pressure for use in the calibration. The gas regulator 74 may be of any type that is compatible with a step-down pressure adjustment. Also the gas regulator 74 is compatible with the gas being used, alcohol being a flammable and reactive compound in sufficiently high concentrations.

The gas control valve 76 is a valve for the control of a specified amount of gas from the gas cylinder 44 to the sample flow tube 100 or equivalent component. The gas control valve 76 is connected to the gas regulator 74. The gas control valve 76 may be of any type capable of enabling the controlled release of gas from the gas cylinder 44 for the period of time specified by the user and/or dictated by the calibration procedure. Examples of gas control valves 76 suitable for such a purpose include, but are not limited to, solenoidal valves, mechanical valves, pneumatic valves, etc. The operation of the gas control valve 76 may be controlled by the microcontroller 52 mounted on the motherboard 50, which receives commands from the device computer 110 during the calibration procedure.

The check valve 78 is used to prevent the backflow of air or other gasses into the gas delivery system 70 which may cause contamination. Any form of check valve 78 or equivalent may be included, including but not limited to ball check valves, diaphragm check valves, stop-check valves, lift-check valves, in-line check valves, or other similar devices known in the art.

In this embodiment, the gas delivery systems 70 and 71 are each operatively connected to a T-coupler 79, which is operatively connected with the sample flow tube 100. The sample flow tube 100 may be any form of suitable tubing or conduit, such as nonreactive tubing for directing the flow of gas from the T-coupler 79 to the IID 12. The sample flow tube 100 may include a connector 102 that enables a connection to a breath receiving port 16 of the IID 12.

The sample flow tube 100 may be, for example, a flexible plastic, rubber, nylon or metal hose, or any other suitable device known in the art, related art, or developed later.

Further as shown in FIGS. 1 and 2, the device computer 110 may be any form of computer components for executing the calibration procedures described herein. In this case, for simplicity, the device computer 110 is a separate laptop computer (or, alternatively, a desktop computer, tablet computer, etc.). In another embodiment, the microcontroller 52 described above might be used, with or without other processing components, memory chips, etc. Any equivalent construction known in the art may be utilized.

The device computer 110 has a computer processor 112 and a computer memory 114 with a calibration program 116 installed on the computer memory 114 of the device computer 110 for receiving the data from the IID 12, calibrating the IID 12, and generating confirmation data that the IID 12 was calibrated. Additionally, the calibration program 116 is capable of transmitting a calibration date and or other unique identifier to the IID 12.

In the present embodiment, once the IID 12 is operably connected to the data port 54 of the IDCCS 10, the calibration program 116 downloads from the IID 12 the client and device data. The client and device data may be stored in the computer memory 114 (e.g., in a local database 118). In this embodiment, the local database 118 is operably installed on the device computer 110, on the computer memory 114 of the device computer 110, or another equivalent memory device. The computer memory 114 may comprise any computer-readable medium known in the art, related art, or developed later including, for example, a single processor or multiple processors operatively connected together, volatile memory (e.g., RAM), non-volatile memory (e.g., flash, etc.), disk drive, etc., or any combination thereof.

In the present embodiment, the calibration program 116 transmits instructions via the data port 54 to initiate and/or direct the IID 12 through the calibration process. Various data inputs, such as those described herein, are taken into account to fully automate the process, and to generate the calibration and test data confirming proper calibration of the IID 12. The calibration and test data is stored in the local database 118. In the present embodiment, the calibration program 116 transmits a new calibration date to the IID 12 only after confirmation has been received following a successful calibration of the IID 12.

The information stored on the local database 118 includes, but is not limited to, the customer's (person being monitored by the IID 12) name, IID 12 unit serial number (both handset and vehicle blocking system), vehicle information such as year, make, model, and vehicle identification number ("VIN"), and prior test results (e.g., prior test results, BrAC levels, information about any missing tests, if the IID 12 has lost power, and any other related information). The data is cross-referenced with existing data in the local database for verifying the identity of the customer. In the present embodiment, the device computer 110 is a laptop computer with a monitor 120, and input devices 122 (such as a keyboard and/or touchpad) and interfaced with the calibration unit 20 to control the functions of the elements within the calibration housing 30 and manage the calibration procedure. In other embodiments the device computer 110 could be a tablet, desktop computer, mobile device, or other computer of equivalent function.

As shown in FIG. 2, the IDCCS 10 may also include or operate in communication with a central computer 130 having a computer processor 132 and a computer memory 134 similar to the computer memory 114. The central computer 130 has a central program 136 and a central database 138 operably installed on the computer memory 134 of the central computer 130. The central program 136 of the central computer 130 receives data from the local database 118 (or, in typical embodiments, a large number of such device computers). The data may be updated in real time, or periodically, and may be transmitted in any manner known in the art (e.g., via a direct connection, LAN, Ethernet, USB line, or over a network, where the connection may either be physical or wireless). The data is stored in the central database 138, where it can then be compiled, analyzed, or otherwise used according to the needs of one skilled in the field.

The network may include, for example, one or more of the Internet, Wide Area Networks (WANs), Local Area Networks (LANs), analog or digital wired and wireless telephone networks (e.g., a PSTN, Integrated Services Digital Network (ISDN), a cellular network, and Digital Subscriber Line (xDSL)), radio, television, cable, satellite, and/or any other delivery or tunneling mechanism for carrying data. Network may include multiple networks or sub-networks, each of which may include, for example, a wired or wireless data pathway. The network may include a circuit-switched voice network, a packet-switched data network, or any other network able to carry electronic communications. For example, the network may include networks based on the Internet protocol (IP) or asynchronous transfer mode (ATM), and may support voice using, for example, VoIP, Voice-over-ATM, or other comparable protocols used for voice, video, and data communications.

One of the functions of the central program 136 is to analyze the data received from the calibration unit 20 to determine the state of a fuel cell or any sensor of the IID 12. For example, a systematic drift in the fuel cell data received could indicate a degradation of the fuel cell sensor that could lead to erroneous readings when used by a customer. Once such a drift in readings is determined, the system may function to request or require replacement of the fuel sensor, or any other sensor. The central database 138 serves a number of functions, including backup storage of data in addition to the data stored on the local databases 118 of all connected calibration units 20, allowing cross-referencing of customer data with other data which may not be stored in the local database 118, or allowing cross-referencing of calibration data between other calibration units 20 to perform a diagnostic function or general reliability testing.

Figure 3:
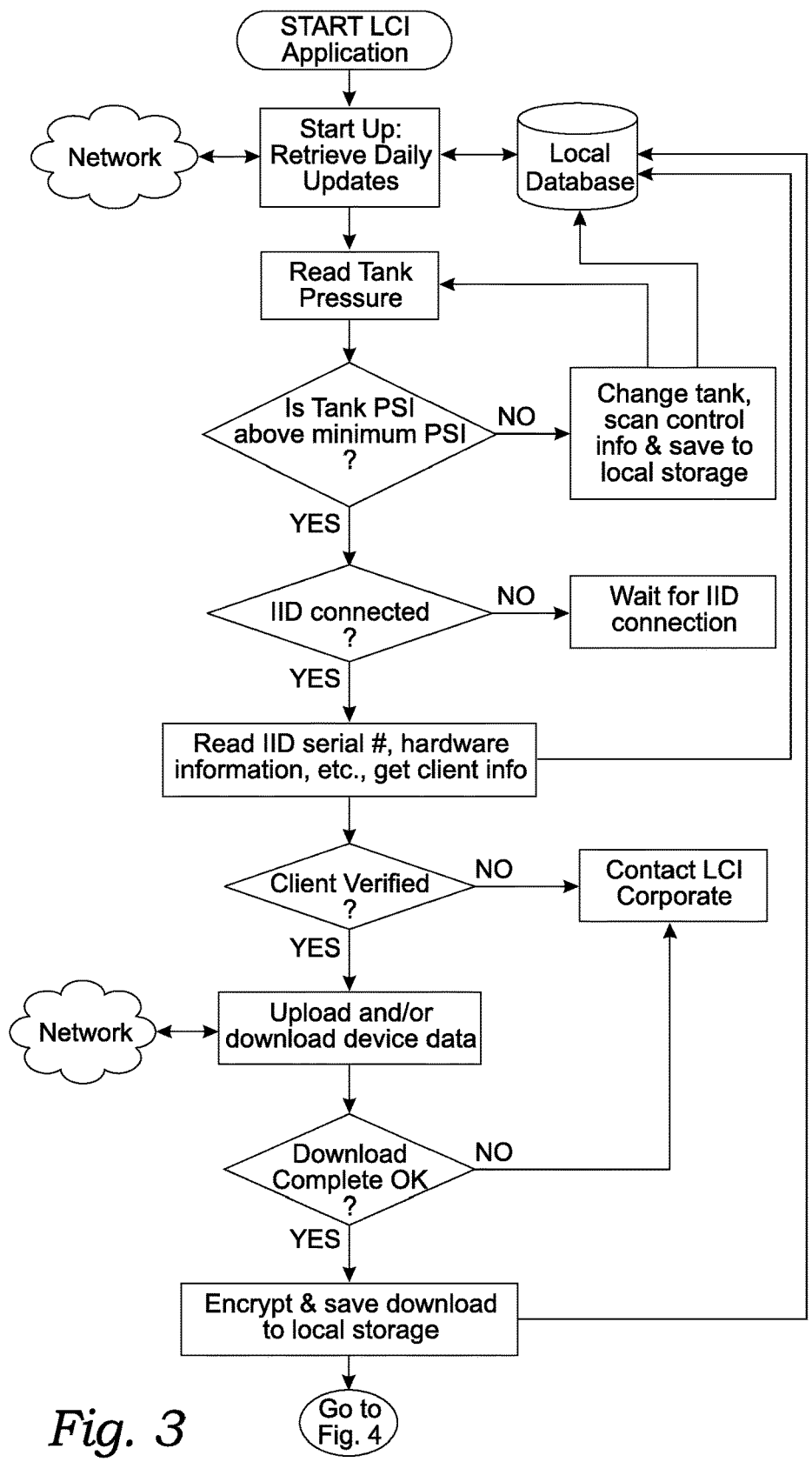
FIG. 3 is a flow diagram of a first part of the operation of the interlock data collection and calibration system of FIG. 1.
Figure 4:
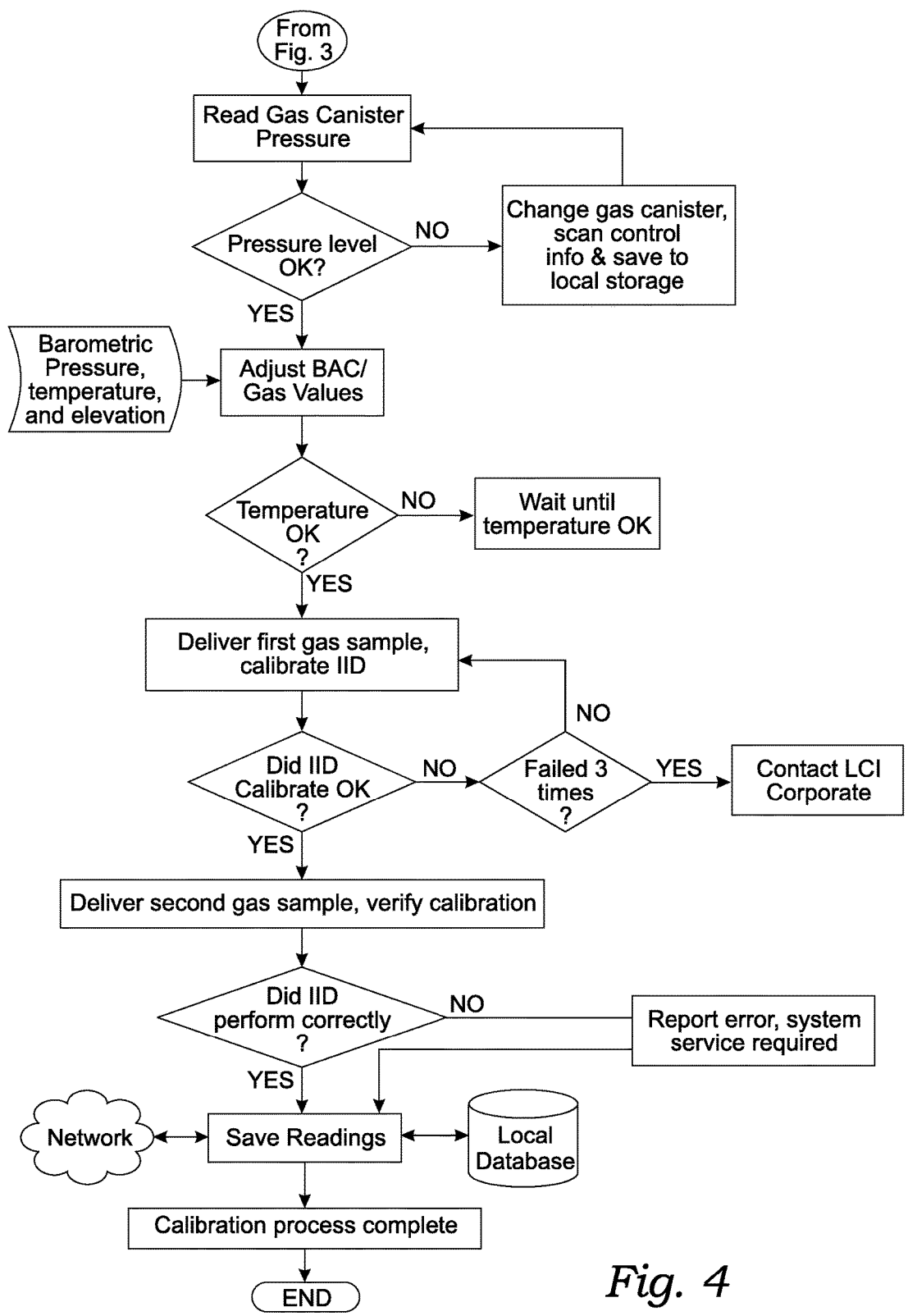
FIG. 4 is a flow diagram of a second part of the operation of the interlock data collection and calibration system of FIG. 1.

FIGS. 3 and 4 are flow diagrams of the operation of the system of FIG. 1. As illustrated in FIGS. 3-4, the calibration procedure is initiated by starting the calibration program 116, typically either by the user pressing the initiation button 56 on the calibration housing 30 or an automatic startup when the system is powered on. This begins the startup phase, where the IDCCS 10 communicates with the network via wireless, landline, 4G internet, etc., and receives daily updates, such as software updates, database updates or other procedures. Any database updates are stored on the local database 118. Also, the IDCCS 10 may send data to and receive data from the central computer 130 such as test results, prior calibration data, or other data regarding the systems usage or status.

In this embodiment, the next step in the calibration procedure is to read the pressure of each of the gas cylinders 44 via an inline pressure transducer such as the inline pressure transducer 72. If the gas cylinders 44 pressure is below a minimum pressure then the user is instructed to remove the low pressure gas cylinders 44, scan the bar code of a replacement gas cylinders 44 which is then stored in the local database 118 and the central database 138, and finally connect a full gas cylinders 44. The bar code or other identification method is stored with the data so that later the particular identification of the gas cylinder may be determined. If the accuracy of the tests performed is ever questioned, it will be possible to determine from the stored data the source of the gas used in the test, and the producer of the gas cylinders 44 can show proof that the gas cylinders 44 contained the correct gas with the correct ethanol content.

Each of the gas cylinders 44 such as the gas cylinder 44 is connected to the leak tight delivery system consisting of the inline pressure transducer 72, an optional pressure relief valve (not shown), the gas regulator 76, the gas control valve 76, and the check valve 78. The gas cylinder 44 pressure is once again determined via the inline pressure transducer 72 to confirm that the pressure is above the required minimum. The pressure of the gas cylinder 45 may be verified in a similar manner. Once this is satisfied, the calibration program 116 confirms that the IID 12 is connected to the data port 54. If the IID 12 is not connected, the calibration program 116 waits until this condition is satisfied before continuing with the procedure.

Once the IID 12 is operably connected to the data port 54, the calibration program 116 receives the IID 12 serial number, hardware information, etc. as well as getting customer information stored on the IID 12. The calibration program 116 then verifies the client identity, for example, by cross-checking the IDCCS 10 identifiers with the IID 12 serial number, pass codes, or other identifiers. If the customer identification cannot be verified, the user is prompted to contact the central office for further instructions. Once the client identity has been verified, device data which was recorded on the IID 12 is downloaded into the computer memory 114 of the device computer 110. An internal check is performed to confirm that the download is complete and without errors, and if incomplete or if errors are present, the user is prompted to contact the central office for further instructions. After a complete and successful download of the device data, the device data is encrypted and saved to the local database 118.

As shown in FIG. 4, the procedure from FIG. 3 continues by once again reading the pressure of the gas cylinder 44 via the inline pressure transducer such as the inline pressure transducer 72. This second pressure check is performed to ensure that there are no leaks in the system or that the gas cylinder 44 is properly connected. Similar second pressure check may be repeated for the second cylinder 45. An unexpected pressure drop could indicate a leak as well as introduce the possibility of external contamination into the gas cylinders 44 or respective gas delivery systems such as the gas delivery system 70. The second pressure check helps to avoid a faulty calibration and giving incorrect test results when the IID 12 is used. If the gas cylinder pressure is below a minimum pressure then the user is instructed to remove the low pressure gas cylinders 44, scan the bar code of a replacement gas cylinder to store the scanned bar code in the local database 118 and the central database 138, and finally connect a full gas cylinders 44. The pressure of each of the gas cylinders 44 is once again read via the respective inline pressure transducers such as the inline pressure transducer 72 to confirm that the pressure is above the required minimum.

Once the gas cylinders 44 pressure is confirmed to be within an acceptable range, the calibration program 116 receives the local barometric pressure from the respective barometer such as the barometer 90, and receives the temperature from the respective temperature sensor such as the temperature sensor 92, and adjusts gas values of the ignition interlock device 12 based upon the temperature data and the pressure data received by the temperature sensor 92 and the barometric pressure sensor 90, correcting for the local barometric pressure and the temperature, which may vary from location to location depending on the weather conditions and/or elevation. As noted above, in alternative embodiments this information may be manually inputted, or otherwise supplied (e.g., via the Internet, or other form of network, or other electronic or mechanical method), either prior to or during calibration, to avoid the requirement of having the barometer and/or the thermometer. After correcting for the pressure and the temperature, the calibration program 116 may also check to make sure that the temperature is within an acceptable range. If the temperature is not in an acceptable range, the calibration procedure will stop and the device will wait until the temperature is within the acceptable range before continuing.

The calibration program of the SYSTEM 10 then directs the gas delivery systems 70 to open to deliver a first sample gas from the gas cylinder 44 to the IID 12 via the sample flow tube 100 for calibrating the IID 12 at the first alcohol concentration (in this case, 0.08 g/dL). The gas delivery systems 70 is then closed, once the calibration procedure is complete.

In one embodiment, after the IID 12 calibration is initially performed, a further diagnostic may be run to determine if the calibration was successful. If not, then the calibration may be repeated up to three times, re-running the diagnostic after each attempt. In the event that there are three failures in a row, the user is prompted to contact the central office for instructions.

The IDCCS 10 then provides a second sample gas to the IID 12 to verify that the IID 12 is correctly calibrated. The calibration program of the IDCCS 10 then directs the gas delivery systems 71 to deliver a second sample gas having a second alcohol concentration (in this case, of 0.02 g/dL) from the gas cylinder 45, so as to verify that the IID 12 is correctly calibrated. If the IID 12 correctly reads the alcohol concentration of the second sample gas, this verification may also be saved and reported, to confirm that the calibration was successful.

In one embodiment, when the first sample gas is delivered to the IID 12, the fuel sensor in the IID 12 is checked to determine a current utilized by the fuel sensor when in use with respect to the gas cylinder 44. Over time, the current data may be analyzed to determine the status of the sensor of the IID 12. If deterioration is found in the IID 12 (e.g., a drop-off in current, or a slower deterioration over time that reaches a predetermined level), the IID 12 may be removed from service and replaced with new one. If the IID 12 is performing at acceptable levels, the IID 12 may remain in service, and the data regarding the acceptable function of the sensor of the IID 12 is stored in the system for future reference. At this point the calibration of the IDCCS 10 is complete and the IID 12 is ready to be used by the customer.

FIG. 5 is a perspective view of an alternative embodiment of the gas sample delivery system 69 of FIG. 1. In this embodiment, the sample flow tube 100 may be connected to the gas delivery system 70 of the IID 12 via a dilution air delivery system 150, which adds a predetermined amount of atmospheric air (or other suitable gas) to vary the alcohol concentration (e.g., 0.08 g/dL) in the first sample gas, thereby providing a source of a second sample gas of a lower concentration, and thereby eliminating the need for an additional gas cylinder such as the gas cylinder 45 shown in FIG. 1. In this embodiment, the dilution air delivery system 150 is a venturi vacuum pump 150, as illustrated in FIG. 5.

The venturi vacuum pump 150 allows to selectively add a predetermined amount of fluid (e.g., air) to change the alcohol concentration of the gas being introduced into the sample flow tube 100. The venturi vacuum pump 150 may be a compressed air vacuum pump including a first chamber 152 and a second chamber 155 separated by a restricted neck 154. The first chamber 152 includes an inlet port 156 for injecting the gas from the gas delivery system 70, and the second chamber 155 includes an outlet port 158 coupled to the IID 12 via a suitable interface media such as the sample flow tube 100. An air inlet aperture 153 into the first chamber 152 is selectively opened or closed with a valve 160 having an air intake 162.

The venturi vacuum pump 150 operates on the principle of the Venturi effect. Upon being connected to the gas cylinder via, e.g., a sample flow tube, the venturi vacuum pump 150 may receive compressed gas containing a predetermined alcohol concentration from the gas cylinder into the first chamber 152 via the inlet port 156. A lower pressure is generated in the first chamber 152, thereby drawing air into the first chamber 152 through the valve 160.

In this embodiment, gas from the gas cylinder 44 may be used directly to provide the first sample gas (i.e., the valve 160 of the venturi vacuum pump 150 is closed, so that the gas is not diluted). Then, when the second sample gas is required, the valve 160 is opened, so that the gas is diluted by the air being drawn through the valve 160, to provide the second sample gas having a lower concentration of alcohol. One ordinarily skilled in the art will understand that the initial alcohol concentration, e.g., 0.08 g/dL, of the gas may be varied to different lower alcohol concentrations, e.g., 0.02 g/dL, by diluting the gas from the cylinder to a particular extent. Alternatively, the valve 160 may be connected to a gas source having a higher alcohol concentration for raising the alcohol concentration, although this would add to the expense of the system, so this approach is not currently favored, although it does remain within the scope of the present invention.

As used in this application, the terms computer, processor, memory, and other computer related components, are hereby expressly defined to include any arrangement of computer(s), processor(s), memory device or devices, and/or computer components, either as a single unit or operably connected and/or networked across multiple computers (or distributed computer components), to perform the functions described herein. Also, the term "ignition interlock device" and related terms are broadly defined to include similar and equivalent devices such as breathalyzers, portable breath test devices (PBT), and other similar or equivalent devices.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. An interlock calibration system comprising:
    an ignition interlock device including a computer processor and a computer memory storing a program; and
    a calibration station including a device computer and a gas sample delivery system that includes a first cylinder of compressed alcohol sample gas and a second cylinder of compressed alcohol sample gas, the first cylinder of compressed alcohol sample gas providing a first sample gas to the ignition interlock device, and the second cylinder of compressed alcohol sample gas providing a second sample gas to the ignition interlock device, the first sample gas having a different alcohol concentration than the second sample gas,
    wherein the computer processor of the ignition interlock device is configured to execute the program and cause the ignition interlock device to use the first sample gas to calibrate the ignition interlock device, and to use the second sample gas to determine whether the calibration of the ignition interlock device was successful.

2. The interlock calibration system of claim 1, wherein the calibration station further includes a data port operably connected with the device computer for enabling data from the ignition interlock device to be transmitted to the device computer.

3. The interlock calibration system of claim 1, wherein each of the first alcohol concentration and the second alcohol concentration are greater than or equal to 0.02 g/dL and less than or equal to 0.15 g/dL.

4. An interlock calibration system comprising:
    an ignition interlock device including a computer processor and a computer memory storing a program; and
    a calibration station including a device computer, a first gas cylinder prefilled with a first compressed sample gas having a first alcohol concentration, and a second gas cylinder prefilled with a second compressed sample gas having a second alcohol concentration that is different than the first alcohol concentration,
    wherein the computer processor of the ignition interlock device is configured to execute the program and cause the ignition interlock device to receive the first compressed sample gas from the first gas cylinder, to use the first compressed sample gas to calibrate the ignition interlock device, to receive the second compressed sample gas from the second gas cylinder, and to use the second compressed sample gas to determine whether the calibration of the ignition interlock device was successful.

5. The interlock calibration system of claim 4, wherein each of the first alcohol concentration and the second alcohol concentration are greater than or equal to 0.02 g/dL and less than or equal to 0.15 g/dL.

6. The interlock calibration system of claim 4, wherein the calibration station further includes:
    a data port operably connected with the device computer for enabling data from the ignition interlock device to be transmitted to the device computer.

7. An interlock calibration system comprising:
    an ignition interlock device including a computer processor and a computer memory storing a program; and
    a calibration station including a device computer a gas sample delivery system that includes a first cylinder of compressed alcohol sample gas a second cylinder of compressed alcohol sample gas, and a common sample flow tube extending between the gas sample delivery system and the ignition interlock device, the first cylinder of compressed alcohol sample gas providing a first sample gas to the ignition interlock device via the common sample flow tube extending between the gas sample delivery system and the ignition interlock device and the second cylinder of compressed alcohol sample gas for providing a second sample gas to the ignition interlock device via the common sample flow tube extending between the gas sample delivery system and the ignition interlock device, the first sample gas having a different alcohol concentration than the second sample gas, wherein the computer processor of the ignition interlock device is configured to execute the program and cause the ignition interlock device to use the first sample gas to calibrate the ignition interlock device, and to use the second sample gas to determine whether the calibration of the ignition interlock device was successful.

8. The interlock calibration system of claim 7, wherein the calibration station further includes a data port operably connected with the device computer for enabling data from the ignition interlock device to be transmitted to the device computer.

9. The interlock calibration system of claim 7, wherein each of the first alcohol concentration and the second alcohol concentration are greater than or equal to 0.02 g/dL and less than or equal to 0.15 g/dL.

\* \* \* \* \*